United States Patent [19]

Berkowitz

[11] 4,172,086

[45] Oct. 23, 1979

[54] PROCESS FOR THE MANUFACTURE OF PEROXYCARBOXYLIC ACIDS

[75] Inventor: Sidney Berkowitz, Highland Park, N.J.

[73] Assignee: FMC Corporation, Philadelphia, Pa.

[21] Appl. No.: 782,204

[22] Filed: Mar. 28, 1977

[51] Int. Cl.$^2$ .................. C11C 3/00; C07C 179/10
[52] U.S. Cl. .................. 260/406; 260/413; 260/502 R
[58] Field of Search .............. 260/413 Q, 406, 502 R

[56] References Cited

U.S. PATENT DOCUMENTS

| | | | |
|---|---|---|---|
| 2,377,038 | 5/1945 | Reichert et al. | 260/502 R |
| 2,813,885 | 11/1957 | Swern et al. | 260/406 |
| 2,813,896 | 11/1957 | Krimm | 260/502 R |
| 2,814,641 | 11/1957 | Phillips et al. | 260/502 R |
| 2,877,266 | 3/1959 | Korach et al. | 260/502 R |
| 3,284,491 | 11/1966 | Korach et al. | 260/502 R |
| 3,367,951 | 2/1968 | Nielson et al. | 260/406 |
| 3,494,898 | 2/1970 | Meyer et al. | 260/78.5 |
| 3,845,112 | 10/1974 | Waldmann et al. | 260/502R |
| 3,849,484 | 11/1974 | Hoffmann et al. | 260/502 R |
| 4,071,541 | 1/1978 | Hildon et al. | 260/502 R |
| 4,087,455 | 5/1978 | Prescher et al. | 260/502 R |

FOREIGN PATENT DOCUMENTS 228665 3/1910 Fed. Rep. of Germany .
251802 9/1911 Fed. Rep. of Germany .

OTHER PUBLICATIONS

Preparation, Characterization & Polarographic Behavior of Long Chain Aliphatic Peracids; W. E. Parker et al., J.A.C.S. 77, 4037–4041 (1955).
Aliphatic Diperacids; W. E. Parker et al.; J.A.C.S. 79, 1929–1931 (1957).
New Method for the Direct Preparation of Aromatic & Aliphatic Peroxy Acids; L. S. Silbert et al., J. Org. Chem., 27, 1336–1342 (1962).

*Primary Examiner*—P. E. Konopka
*Attorney, Agent, or Firm*—Robert W. Kell; Frank Ianno

[57] ABSTRACT

Peroxycarboxylic acids are prepared by the oxidation of a fatty acid with an excess of hydrogen peroxide in the presence of a strong acid catalyst. The yield is improved and the reaction time is reduced by intimately dispersing throughout the reaction mixture an inert water immiscible solvent for the peroxycarboxylic acid. The product may be recovered in crystalline form from the solvent phase.

41 Claims, No Drawings

PROCESS FOR THE MANUFACTURE OF PEROXYCARBOXYLIC ACIDS

This invention comprises a safe, rapid and efficient process whereby peroxycarboxylic acids may be obtained in good yield and in crystalline form. The use of such peracids as oxidation agents, disinfecting agents, bleaching agents and catalysts has long been known. The diperoxycarboxylic acids in particular possess superior bleaching and germicidal properties for textile and home laundry applications.

The highly reactive aliphatic peracids were first prepared and evaluated by D'Ans and co-workers during the first two decades of the twentieth century. D'Ans prepared mainly performic, peracetic, perpropionic and perbutyric acids by reaction of hydrogen peroxide with the appropriate acid or anhydride in the presence of catalytic quantities of inorganic acids. The preparation of aliphatic peracids containing six or more carbon atoms presented certain difficulties for the D'Ans procedure. The low solubility of the parent acid in aqueous hydrogen peroxide prevents intimate contact between the reactants and causes the reaction to proceed at a very slow rate. To overcome those solubility problems, Parker, Swern & Krimm describe the preparation of both short and long chain mono- and diperacids using either concentrated sulfuric acid or methane sulfonic acids as the reaction medium. Among the peroxyacids prepared by these procedures was diperoxyazelaic acid.

An alternative process in which water was removed from the reaction at 40°-50° C. by using an azeotropic agent such as alkyl acetates and chloroform was described by Phillips et al. This method worked for peracetic and perpropionic acid but failed to form longer chain peroxy acids.

It is known to prepare percarboxylic acids by reacting a monocarboxylic acid with 30% hydrogen peroxide in the presence of sulfuric acid as catalyst. This reaction is described by Krimm in U.S. Pat. No. 2,813,896. The reaction of hydrogen peroxide with the organic acid is, however, a strongly exothermic reaction that can occur with explosive violence. Krimm, in the patent identified above, describes an improvement over this prior art process in the use of an increased amount of sulfuric acid, e.g., one mole of sulfuric acid to 3 or 4 moles of the hydrogen peroxide. Krimm describes for the first time the reaction to form peroxy acids of aliphatic dicarboxylic acids such as azelaic and sebacic acids.

The Korach U.S. Pat. No. 2,877,266 relates to the preparation of peracetic acid by mixing acetic acid with hydrogen peroxide, preferably in highly concentrated form, e.g., 90% $H_2O_2$. The reaction is driven to completion by distilling off the water present in the reaction mixture azeotropically as a mixture of the water and an inert water immiscible solvent that will form an azeotrope with the water present in the reaction mixture. Suitable solvents that are disclosed by Korach as forming water azeotropes which boil below 100° C. are the chlorinated hydrocarbons such as ethylene dichloride and methylene chloride. As the water is removed, the reaction proceeds to completion, or substantially so, and the acetic acid is largely converted to peracetic acid. The process contemplated may be applied to the production of dibasic percarboxylic acids such as maleic, adipic, azelaic and phthalic acids.

Korach, in U.S. Pat. No. 3,284,491 discusses the explosive hazard inherent in the manufacture of percarboxylic acids by the process of his earlier U.S. Pat. No. 2,877,266 and describes as an improvement over his earlier process the addition of an inert water soluble organic solvent to the reaction mixture in amounts sufficient to prevent the formation of a separate aqueous phase.

Parker has described the preparation and behavior of long chain aliphatic peracids using concentrated sulfuric acid as a solvent for the aliphatic acid and hydrogen peroxide. Jour. Am. Chem. Soc. 77, 4037-41 (1955). The application of this reaction to the preparation of aliphatic diperacids in good yields is also described by Parker. Jour. Am. Chem. Soc. 79, 1929-1931 (1957).

Silbert et al replace sulfuric acid with methane sulfonic acid in the preparation of aromatic and aliphatic peroxy acids. J. Org. Chem. 27, 1336-1342 (1962).

In accordance with the present invention, an aromatic or aliphatic organic acid is reacted with an excess of hydrogen peroxide in the presence of a suitable strong acid catalyst, the amount of the acid catalyst being sufficient to tie up the by-product water by its hydroscopic effect or by chemical reaction. It has now been discovered that the reaction time can be greatly reduced and the yield of peroxycarboxylic acid increased by intimately dispersing throughout the aqueous reaction mixture an inert water-immiscible solvent for the peroxycarboxylic acid. The reaction mixture may be separated into two phases at the end point of the reaction, an aqueous phase and a solvent phase; and the product recovered in essentially pure crystalline form from either the aqueous phase or the solvent phase.

It is an advantage of the present invention that the oxidation reaction is performed in a rapid, safe and easily controlled operation. The hazardous conditions inherent in the prior art procedures are greatly reduced.

Another advantage of the process of the present invention is a lower capital investment in plant facilities as the large and expensive reactors required by the prior art process are not required.

Still another advantage of the present invention is a substantial reduction in the costs of manufacturing and pollution control.

The formation of a peroxy acid from a carboxylic acid and hydrogen peroxide is an equilibrium process which proceeds in the aqueous phase in accordance with the overall equation:

$$RCO_2H + H_2O_2 \rightleftharpoons RCO_3H + H_2O \qquad (1)$$

As disclosed in U.S. Pat. No. 2,877,266 granted to Malcolm Korach, it is possible to produce a percarboxylic acid in greater yield and to drive the reaction to a greater degree of completion by introducing into the reaction mixture, before or during distillation, a water immiscible solvent which forms an azeotrope with water. In consequence, as the azeotrope is distilled removing the water, the reaction continues to move toward the production of the peroxycarboxylic acid and therefore substantial yields of the peroxycarboxylic acid, based upon the theoretical yield from the carboxylic acid precursor, can be obtained.

The improvement in the process disclosed herein is obtained by shifting the equilibrium reaction illustrated by equation 1 above to the right, not by the removal from the reaction mixture of by-product water as practiced in the prior art processes, but by selective removal from the aqueous reaction mixture phase, of the percarboxylic acid as it is formed. This is accomplished by intimately dispersing throughout the aqueous phase of the reaction mixture during the course of the reaction an inert water immiscible solvent for the peroxycarboxylic acid. The solvent is added at the start of the reaction and intimately dispersed throughout the reaction mixture by agitation until the reaction is complete.

The reaction of aliphatic peracids is rapidly accelerated by strong acids such as $H_2SO_4$ in accordance with the following equation:

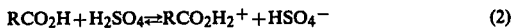

$$RCO_2H + H_2SO_4 \rightleftharpoons RCO_2H_2^+ + HSO_4^- \quad (2)$$

$$RCO_2H_2^+ + H_2O_2 \rightleftharpoons RCO_3H + H_3O^+ \quad (3)$$

Sufficient acid must be present to effect reactions 2 and 3 and to tie-up the by-product water. Mole ratios of carboxylic acid/acid catalysts from 1:1.3 to 1:5 can be used, with optimum results obtained at a carboxylic acid/acid catalyst ratio of 1:2 to 1:3. The reaction will proceed in a like manner with other suitable strong acids such as trifluoromethanesulfonic acid, methanesulfonic acid, toluenesulfonic acid, etc.

The acid catalyst that is preferred for the manufacture of aliphatic peroxycarboxylic acid is sulfuric acid and it has been found that the reaction is extremely sensitive to the acid strength. Satisfactory rates have been achieved at sulfuric acid concentrations in the range of 95% up to 30% oleum, with maximum rates obtained at sulfuric acid concentrations of 100% to 10% oleum. Methanesulfonic acid is also a suitable catalyst for the process of the present invention and is preferred over sulfuric acid for the manufacture of aromatic percarboxylic acids because sulfuric acid may sulfonate the benzene ring.

In order to achieve complete conversion of the organic acid to the corresponding peroxy acid at least stoichiometric quantities of $H_2O_2$ per mole of starting organic acid are necessary. Thus, 2 moles of $H_2O_2$ per mole of a dibasic acid are required according to the following equation:

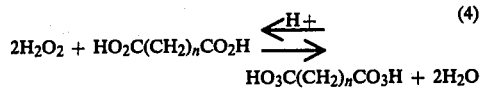

$$2H_2O_2 + HO_2C(CH_2)_nCO_2H \xrightarrow{H+} HO_3C(CH_2)_nCO_3H + 2H_2O \quad (4)$$

wherein n=7 to 18.

Molar ratios of dibasic acid/$H_2O_2$ from 1:2 to 1:5 can be used with optimum results obtained at dibasic acid/$H_2O_2$ ratios of 1:2 to 1:3. At lower molar ratios of dibasic acid/$H_2O_2$ (1:1) mixtures of mono, diperoxy acid and starting carboxylic acids are obtained.

In order to effect the reaction described above, the choice of solvents is important. The solvent should be
(1) essentially water immiscible,
(2) unreactive toward high strength $H_2O_2$, peracids and strong acid catalysts,
(3) show only limited solvent capacity for the parent carboxylic acid at reaction temperature, while dissolving most of the resulting peroxy acid as it forms,
(4) non-toxic, and
(5) relatively inexpensive.

Aromatic hydrocarbons such as benzene and toluene may be used as a solvent and the halogenated hydrocarbons, both aliphatic and aromatic, satisfy the above requirements. Methylene chloride is particularly preferred as a water immiscible solvent for the diperoxycarboxylic acids.

The rate of formation of the peroxycarboxylic acid from the parent acid in the solvent system is a function of reaction temperature and acid catalyst concentration. With $C_{12}$ and higher dibasic acids, the reaction kinetics are extremely sensitive to acid catalyst strength. For example, in refluxing methylene chloride, the rate of formation of diperoxydodecanedioic acid was markedly increased by increasing concentration from 96% $H_2SO_4$ to 5% oleum. Under optimum conditions, essentially complete conversions are achieved in a matter of minutes.

The reaction temperatures are a function of the carboxylic acid employed. Azelaic and sebacic acid required temperatures of 20°–30° C., while $C_{11}$, $C_{12}$ and higher dibasic acids required reaction temperatures of 40°–60° C. to achieve maximum conversions.

The reaction of an organic acid with $H_2O_2$ in the two phase system described above is a mildly exothermic reaction which is easily controlled. The use of a low boiling solvent such as methylene chloride or chloroform acts as a built-in heat sink and quench system.

Many of the organic acids which are oxidized in accordance with the present invention are insoluble in both the aqueous and the solvent phase of the reaction mixture and are present in the reaction mixture as a slurry. The process of the present invention proceeds efficiently at slurry concentrations up to about 20 weight percent organic acid. For ease of operation and particularly for efficient agitation it is preferred to employ slurry concentrations of about 8–12 weight percent organic acid in the total reaction mixture.

The reaction product can be removed from the reaction mixture as essentially pure peroxyacid by (a) separation of the organic phase from which the product is isolated by crystallization or evaporation of the solvent or (b) additional water may be added to the reaction mixture after completion of the reaction, the solvent removed by distillation, and the product isolated from the remaining aqueous phase.

The diperoxy acids that crystallize from the organic phase are large, well defined crystals which filter rapidly. It has also been found quite unexpectedly that the diperoxyazelaic acid and diperoxysebacic acid crystals formed upon addition of water at the reaction end point are very large and easily filterable. The crystal size can be controlled by the amount of acid catalyst. Very large crystals (200×150μ) are obtained at mole ratios of azelaic acid/$H_2SO_4$ of 1:2. Smaller crystals (80×75μ) are obtained at mole ratios of azelaic acid/$H_2SO_4$ of 1:1.5.

This invention is illustrated by the examples given below wherein all quantities are expressed in parts by weight.

EXAMPLE 1

This example demonstrates the production of diperoxydodecanedioic acid (DPDA) using methylene chloride solvent. Eleven hundred and fifty parts (5.0 moles) of dodecanedioic acid (assay 99+%) is suspended in 16,032 parts (12,000 parts by volume) of methylene chloride contained in a reaction vessel equipped with a Teflon coated mechanically agitated stirrer, thermometer, and condenser. One thousand four hundred and seventy parts (15 moles) of sulfuric acid (100%) are added to the reaction mixture which is then heated to 35° C. Hydrogen peroxide (70%, 610 parts, 12.5 moles) is added rapidly over 1-2 minutes, during which time the temperature increases to 38° C. The reaction mixture is then heated to reflux (41° C.) and maintained at reflux for 30 minutes. At this point, 22,000 parts of cold water are added to the reaction mixture. The solvent is distilled off at atmospheric pressure. The aqueous layer containing the white crystalline product filters rapidly. The solids are washed to remove residual sulfuric acid and hydrogen peroxide and dried at 30° C./20 mm. Hg. Total solids recovered from the reaction mixture are identified as diperoxydodecanedioic acid by active oxygen, melting point and X-ray diffraction. The total yield is 1,270 parts of the produce (assay 99.0% purity) which is equivalent to a 96% yield based on starting dodecanedioic acid.

EXAMPLE 2

This example demonstrates the production of diperoxydodecanedioic acid (DPDA) using methylene chloride solvent from which the product is obtained by crystallization. The same reactor and conditions are employed as described in Example 1. At the end of the reaction (30 minutes), the solvent layer is separated from the aqueous layer and the organic phase is slowly cooled to −10° C. during which time the DPDA crystallizes from solution. The product, which filters rapidly, is washed and dried. The aqueous phase is diluted with water to precipitate the small amount of dissolved DPDA which is filtered, washed and dried. Total yield of diperoxydodecanedioic acid is 1,306 parts (assay 96.3% purity) which is equivalent to a 96.5% yield based on starting dodecanedioic acid.

EXAMPLES 3-7

Diperoxydodecanedioic acid is prepared by the procedure described in Example 2, using the solvent identified in Table I. The yield of DPDA varies from 92.5% to 95.8%.

EXAMPLES 8-13

Examples 8-13 illustrate the effect of $H_2SO_4$ strength on the reaction rate for the formation of diperoxydodecanedioic acid (DPDA) in methylene chloride solvent following the general procedure of Example 1. In Examples 8-13 (kinetic runs), the hydrogen peroxide is added to the reaction vessel as rapidly as possible. In Examples 12 and 13, the hydrogen peroxide is added to the reaction through the condenser. In each example, the reaction is quenched with cold water 5 minutes after the addition of hydrogen peroxide. The conversion to DPDA after 5 minutes is listed for comparison in Table II.

EXAMPLE 14

The procedure described in Example 1 is repeated substituting for the sulfuric acid catalyst 15 moles (1,442 parts) of methanesulfonic acid. The yield of diperoxydodecanedioic acid (DPDA) is 93% based on starting dodecanedioic acid.

EXAMPLE 15

The procedure described in Example 2 is repeated substituting for the sulfuric acid catalyst 15 moles (2,251 parts) of trifluoromethanesulfonic acid. The yield of diperoxydodecanedioic acid is 95.5% based on starting dodecanedioic acid.

EXAMPLE 16

This example demonstrates the production of diperoxyazelaic acid (DPAA) using methylene chloride solvent. Nine hundred forty parts (5 moles) of azelaic acid (assay 99+%) are suspended in 1,632 parts (12,000 parts by volume) of methylene chloride contained in a reaction vessel equipped with a TEFLON®-coated, mechanically-agitated stirrer, thermometer, and condenser. One thousand twenty parts (10 moles) of sulfuric acid (96%) are added. Hydrogen peroxide (70%, 730 parts, 15 moles) is then added slowly over 2-3 minutes while maintaining the temperature at 25°-28° C. Upon addition of the peroxide, the reaction becomes homogeneous and after a few minutes, a white oil phase develops. Stirring is continued for a total of 30 minutes. At this point, 12,500 parts of cold water are added to the reaction mixture. The white oil crystallizes to large, well defined crystals (200×150μ). The solvent is flashed off under reduced pressure and the water layer is filtered, the filtration being extremely rapid. The solids are washed with water to remove residual acids and hydrogen peroxide and dried under vacuum at 25° C. Total solids recovered from the reaction mixture are identified as essentially pure diperoxyazelaic acid by active oxygen, melting point and X-ray diffraction. The total yield is 1,050 parts or 95.4% based on starting azelaic acid.

EXAMPLES 17-23

Diperoxyazelaic acid (DPAA) is prepared by the general procedure described in Example 16. The amounts of hydrogen peroxide, azelaic acid, and acid catalyst; the type of acid catalyst; and the reaction time and temperature are varied to evaluate the effect of these parameters on product yield. The results are summarized in Table III.

EXAMPLES 24-30

Diperoxyazelaic acid (DPAA) is prepared by the general procedure described in Example 16, substituting an equal volume of other organic solvents for the methylene chloride used in that example. The effect of solvent substitution on product yield and crystal size is summarized in Table IV.

EXAMPLE 31

This example demonstrates the production of diperoxysebacic acid. The procedure and equipment employed are the same as described in Example 1. One thousand and ten parts (5 moles) of sebacic acid are suspended in 1,737 parts, (13,000 parts by volume) of methylene chloride. To this suspension is added 1,020 parts (10 moles) of sulfuric acid (96%). The reaction mixture is heated to reflux. Six hundred and ten parts of hydrogen peroxide (70%, 12.5 moles) is added rapidly to the reaction mixture which is then stirred at reflux (40° C.) for one hour. The reaction product is recovered as described in Example 1. The total yield of essentially pure diperoxysebacic acid is 96% based on starting sebacic acid.

EXAMPLE 32

This example demonstrates the production of a C-14 dibasic peracid, diperoxytetradecanedioic acid. The procedure and reaction vessel employed are the same as described in Example 1. Twelve hundred and ninety parts (5 moles) of 1,12-dodecanedicarboxylic acid are suspended in 19,480 parts (13,000 parts by volume) of chloroform. To this suspension is added 1,530 parts (15 moles) of sulfuric acid (96%). The reaction mixture is heated to 50° C. and 610 parts of hydrogen peroxide (70%, 12.5 moles) are added rapidly. The reaction is maintained at 50° C. for 60 minutes. The layers are then separated, and the organic phase is cooled to −15° C. The crystals of diperoxytetradecanedioic acid are filtered, washed and dried. The total yield of diperoxytetradecanedioic acid is 94.1%.

EXAMPLE 33

Seven hundred and eighty-two parts (5 moles) of metachlorobenzoic acid is suspended in 26,338 parts (18,500 parts by volume) of methylene chloride. To this suspension is added 1,440 parts (15 moles) of methanesulfonic acid. Then 36,364 parts of hydrogen peroxide (7.5 moles, 70%) are added rapidly, and the reaction mixture is heated to reflux (40°–41° C. for one hour).

At the end of one hour, 12,500 parts of cold water are added and the solvent is distilled off. Upon cooling to room temperature, the product is recovered from the aqueous solution. The yield of the m-chloroperbenzoic acid recovered, 646 parts by weight, is 80.6% based on the starting acid.

EXAMPLE 34

Twelve hundred and eighty-two parts (5 moles) of palmitic acid is suspended in 21,355 parts (1,500 parts by volume) of methylene chloride. To this suspension is added 1,020 parts (10 moles) of 96% sulfuric acid. Then 364 parts of hydrogen peroxide (7.5 moles, 70%) are added rapidly and the reaction mixture is stirred at 32° C. for 60 minutes. At the end of one hour, 18,500 parts of water are added, and the methylene chloride is distilled off. The total yield of peroxypalmitic acid (99+% assay) is 1,290 parts, or 94.9% based on the palmitic acid.

Although the present invention has been described with reference to the specific details of certain embodiments, it is not intended that such details shall be regarded as limitation upon the scope of the invention except insofar as included in the accompanying claims.

TABLE I

DPDA PREPARATIONS - ALTERNATE SOLVENTS

| Example | Solvent | Parts By Weight | Reaction Temp. °C. | Time (min.) | % Yield DPDA | Remarks |
|---|---|---|---|---|---|---|
| 3 | chloroform | 17,981 | 50 | 30 | 95.8 | |
| 4 | 1,2-dichloroethane | 15,084 | 50 | 30 | 95.1 | |
| 5 | trichlorotrifluoroethane (Freon 113) | 17,196 | 48 | 30 | 93.5 | |
| 6 | Monochlorobenzene | 13,279 | 30 | 60 | 93.6 | Reaction at |
| 7 | 1,1,2,2-tetrachloroethane | 19,200 | 30 | 60 | 92.5 | reflux |

TABLE II

THE EFFECT OF $H_2SO_4$ STRENGTH OF DPDA CONVERSION IN $CH_2Cl_2$

| Example | Acid Used | Mole Ratio DDA | $H_2O_2$ | Acid | Temp. °C. | Time (min) | % Yield DPDA | Remarks |
|---|---|---|---|---|---|---|---|---|
| 8 | 96% $H_2SO_4$ | 1 | 2.5 | 3.0 | 41 | 5 | 82.5 | Kinetic Run |
| 9 | 5% oleum | 1 | 2.5 | 3.0 | 41 | 5 | 88.2 | Kinetic Run |
| 10 | 10% oleum | 1 | 2.5 | 3.0 | 41 | 5 | 88.1 | Kinetic Run |
| 11 | 30% oleum | 1 | 2.5 | 3.0 | 41 | 5 | 72.5 | Kinetic Run |
| 12 | 65% oleum | 1 | 2.5 | 3.0 | 41 | 5 | 30.5 | Sufficient $SO_3$ present to tie-up all $H_2O$ |
| 13 | Liquid $SO_3$ | 1 | 2.5 | 4.2 | 41 | 5 | 18.1 | Sufficient $SO_3$ present to tie-up all $H_2O$ |

TABLE III

EFFECT OF SEVERAL VARIABLE ON DPAA FORMATION

| Ex. | Acid Catalyst | Mole Ratio AA$^{(a)}$ | Ac$^{(b)}$ | $H_2O_2$ | Reaction Temp. °C. | Time (min) | % Yield of DPAA | Remarks |
|---|---|---|---|---|---|---|---|---|
| 17 | $H_2SO_4$ | 1 | 2 | 3 | 28 | 60 | 95.2 | Large DPAA crystals 190 × 180μ |
| 18 | $H_2SO_4$ | 1 | 2 | 2.5 | 28 | 45 | 95.1 | Large DPAA crystals 190 × 180μ |
| 19 | $H_2SO_4$ | 1 | 2 | 3 | 38 | 30 | 95.3 | Large DPAA crystals 190 × 180μ |
| 20 | $H_2SO_4$ | 1 | 1.5 | 3 | 28 | 60 | 95.0 | DPAA Crystals are smaller size 80 × 75μ dewatered well |
| 21 | $CH_3SO_3H$ | 1 | 2 | 3 | 28 | 30 | 95.0 | Large DPAA crystals 195 × 180μ |
| 22 | $CH_3SO_3H$ | 1 | 5 | 3 | 26 | 30 | 94.8 | Large DPAA crystals |

TABLE III-continued
EFFECT OF SEVERAL VARIABLE ON DPAA FORMATION

| Ex. | Acid Catalyst | Mole Ratio AA[a] | Mole Ratio Ac[b] | Mole Ratio $H_2O_2$ | Reaction Temp. °C. | Time (min) | % Yield of DPAA | Remarks |
|---|---|---|---|---|---|---|---|---|
| 23 | $CH_3SO_3H$ | 1 | 2 | 3 | 38 | 30 | 95.1 | 195 × 180μ Large DPAA crystals 195 × 180μ |

AA[a] = moles of azelaic acid
Ac[b] = moles of acid catalyst

TABLE IV
DPAA PREPARATIONS - ALTERNATE SOLVENTS

| Example | Solvent | Parts By Weight | % Yield DPAA | Remarks |
|---|---|---|---|---|
| 24 | chloroform | 17,981 | 95 | Solvent distilled off under reduced pressure DPAA crystals were large (190 × 150μ) |
| 25 | carbon tetrachloride | 19,583 | 92 | Solvent distilled off under reduced pressure DPAA crystals were medium (100 × 80μ) |
| 26 | 1,2-dichloroethane | 15,084 | 92 | Solvent decanted, DPAA crystals were large (190 × 150μ) |
| 27 | 1,1,2,2-tetrachloroethane | 19,200 | 95 | Solvent decanted, DPAA crystals were large (190 × 150μ) |
| 28 | monochlorobenzene | 13,279 | 93 | Solvent decanted, DPAA crystals were large (190 × 150μ) |
| 29 | o-dichlorobenzene | 15,658 | 93 | Solvent decanted, DPAA crystals were large (190 × 150μ) |
| 30 | trichlorotrifluoroethane (Freon 113) | 17,196 | 95 | Solvent distilled off, DPAA crystals were large (190 × 150μ) |

What is claimed is:

1. In a process for the manufacture of a peroxycarboxylic acid in crystalline form by the oxidation in an aqueous phase of a carboxylic acid with hydrogen peroxide, the improvement which comprises: conducting the reaction in the presence of a strong acid selected from the group consisting of oleum, sulfuric acid, trifluoromethanesulfonic acid, methanesulfonic acid and toluenesulfonic acid; the amount of said strong acid being in the range of from about 1.3 to about 5 moles for each mole of said carboxylic acid present in the reaction mixture, and intimately dispersing throughout said aqueous phase a sufficient quantity of an inert, water-immiscible solvent for the peroxycarboxylic acid to selectively remove from said aqueous phase the peroxycarboxylic acid as it is formed said solvent having been mixed with the carboxylic acid and the strong acid prior to the addition of the hydrogen peroxide.

2. The process of claim 1 wherein the strong acid is methanesulfonic acid.

3. The process of claim 1 wherein the inert, water-immiscible solvent is monochlorobenzene.

4. The process of claim 1 wherein the water-immiscible solvent is ortho-dichlorobenzene.

5. In a process for the manufacture of a peroxycarboxylic acid in crystalline form by the oxidation in an aqueous phase of a long chain carboxylic acid with hydrogen peroxide, the improvement which comprises: conducting the reaction in the presence of a strong acid selected from the group consisting of oleum, sulfuric acid, trifluoromethanesulfonic acid, methanesulfonic acid and toluenesulfonic acid; the amount of said strong acid being in the range of from about 1.3 to about 5 moles for each mole of said carboxylic acid present in the reaction mixture, and intimately dispersing throughout said aqueous phase a sufficient quantity of an inert, water-immiscible solvent for the peroxycarboxylic acid to selectively remove from said aqueous phase the peroxycarboxylic acid as it is formed said solvent having been mixed with the carboxylic acid and the strong acid prior to the addition of the hydrogen peroxide; separating by decantation the aqueous phase from the water-immiscible solvent; and crystallizing from said solvent the peroxycarboxylic acid.

6. In a process for the manufacture of a diperoxycarboxylic acid in crystalline form by the oxidation in an aqueous phase of a long chain dicarboxylic acid with hydrogen peroxide, the improvement which comprises: conducting the reaction in the presence of a strong acid selected from the group consisting of oleum, sulfuric acid, trifluoromethanesulfonic acid, methanesulfonic acid and toluenesulfonic acid; the amount of said strong acid being in the range of from about 1.3 to about 5 moles for each mole of said carboxylic acid present in the reaction mixture, and intimately dispersing throughout said aqueous phase a sufficient quantity of an inert, water-immiscible solvent for the diperoxycarboxylic acid to selectively remove from said aqueous phase the peroxycarboxylic acid as it is formed said solvent having been mixed with the carboxylic acid and the strong acid prior to the addition of the hydrogen peroxide; separating by decantation the aqueous phase from the water-immiscible solvent; and crystallizing from said solvent the diperoxycarboxylic acid.

7. The process of claim 6 wherein the strong acid is 96% sulfuric acid.

8. The process of claim 6 wherein said diperoxycarboxylic acid is diperoxydodecanedioic acid.

9. The process of claim 6 wherein said diperoxycarboxylic acid is diperoxyazelaic acid.

10. The process of claim 6 wherein said diperoxycarboxylic acid is diperoxysebacic acid.

11. The process of claim 6 wherein said diperoxycarboxylic acid is diperoxytetradecanedioic acid.

12. The process of claim 6 wherein said reaction is carried out at the refluxing temperature of the inert, water-immiscible solvent.

13. The process of claim 6 wherein the inert, water-immiscible solvent is chloroform.

14. The process of claim 6 wherein the inert, water-immiscible solvent is carbon tetrachloride.

15. The process of claim 6 wherein the inert, water-immiscible solvent is 1,2-dichloroethane.

16. The process of claim 6 wherein the inert, water-immiscible solvent is 1,1,2,2-tetrachloroethane.

17. The process of claim 6 wherein the inert, water-immiscible solvent is trichloro-trifluoro ethane.

18. The process of claim 6 wherein the inert, water-immiscible solvent is methylene chloride.

19. In a process for the manufacture of a peroxycarboxylic acid in crystalline form by the oxidation in an aqueous phase of a carboxylic acid with hydrogen peroxide, the improvement which comprises: conducting the reaction in the presence of a strong acid selected from the group consisting of oleum, sulfuric acid, trifluoromethanesulfonic acid, methanesulfonic acid and toluenesulfonic acid; the amount of said strong acid being in the range of from about 1.3 to about 5 moles for each mole of said carboxylic acid, and intimately dispersing throughout said aqueous phase a sufficient quantity of an inert, water-immiscible solvent for the peroxycarboxylic acid to selectively remove from said aqueous phase the peroxycarboxylic acid as it is formed said solvent having been mixed with the carboxylic acid and the strong acid prior to the addition of the hydrogen peroxide; adding water to the reaction mixture at the conclusion of the reaction; distilling off the water-immiscible solvent at a temperature below the decomposition temperature of the peroxycarboxylic acid and separating the peroxycarboxylic acid crystals from the residual aqueous phase.

20. The process of claim 19 wherein the strong acid is methanesulfonic acid.

21. The process of claim 19 wherein said immiscible solvent is monochlorobenzene.

22. The process of claim 19 wherein said immiscible solvent is ortho-dichlorobenzene.

23. In a process for the manufacture of a peroxycarboxylic acid in crystalline form by the oxidation in an aqueous phase of a long chain carboxylic acid with hydrogen peroxide, the improvement which comprises: conducting the reaction in the presence of a strong acid selected from the group consisting of oleum, sulfuric acid, trifluoromethanesulfonic acid, methanesulfonic acid and toluenesulfonic acid; the amount of said strong acid being in the range of from about 1.3 to about 5 moles for each mole of said carboxylic acid present in the reaction mixture, and intimately dispersing throughout said aqueous phase a sufficient quantity of an inert, water-immiscible solvent for the peroxycarboxylic acid to selectively remove from said aqueous phase the peroxycarboxylic acid as it is formed said solvent having been mixed with the carboxylic acid and the strong acid prior to the addition of the hydrogen peroxide; adding water to the reaction mixture at the conclusion of the reaction; distilling off the water-immiscible solvent at a temperature below the decomposition temperature of the peroxycarboxylic acid and separating the peroxycarboxylic acid crystals from the residual aqueous phase.

24. In a process for the manufacture of a diperoxycarboxylic acid in crystalline form by the oxidation in an aqueous phase of a long chain dicarboxylic acid with hydrogen peroxide, the improvement which comprises: conducting the reaction in the presence of a strong acid selected from the group consisting of oleum, sulfuric acid, trifluoromethanesulfonic acid, methanesulfonic acid and toluenesulfonic acid; the amount of said strong acid being in the range of from about 1.3 to about 5 moles for each mole of said dicarboxylic acid present in the reaction mixture, and intimately dispersing throughout said aqueous phase a sufficient quantity of an inert, water-immiscible solvent for the diperoxycarboxylic acid to selectively remove from said aqueous phase the diperoxycarboxylic acid as it is formed said solvent having been mixed with the carboxylic acid and the strong acid prior to the addition of the hydrogen peroxide; adding water to the reaction mixture at the conclusion of the reaction; distilling off the water-immiscible solvent at a temperature below the decomposition temperature of the diperoxycarboxylic acid and separating the diperoxycarboxylic acid crystals from the residual aqueous phase.

25. The process of claim 24 wherein the strong acid is 96% sulfuric acid.

26. The method of claim 24 wherein said diperoxycarboxylic acid is diperoxydodecanedioic acid.

27. The process of claim 24 wherein said diperoxycarboxylic acid is diperoxyazelaic acid.

28. The process of claim 24 wherein said diperoxycarboxylic acid is diperoxysebacic acid.

29. The method of claim 24 wherein said diperoxycarboxylic acid is diperoxytetradecanedioic acid.

30. The process of claim 24 wherein said reaction is carried out in the refluxing temperature of the water-immiscible solvent.

31. The process of claim 23 wherein said immiscible solvent is carbon tetrachloride.

32. The process of claim 23 wherein said immiscible solvent is 1,2-dichloroethane.

33. The process of claim 23 wherein said immiscible solvent is 1,1,2,2-tetrachloroethane.

34. The process of claim 23 wherein said immiscible solvent is trichloro-trifluoro ethane.

35. The process of claim 23 wherein said immiscible solvent is methylene chloride.

36. The process of claim 5 wherein the strong acid is 5% oleum.

37. The process of claim 6 wherein the strong acid is 5% oleum.

38. The process of claim 19 wherein the strong acid is 5% oleum.

39. The process of claim 24 wherein the strong acid is 5% oleum.

40. The process of claim 5 wherein the strong acid is 10% oleum.

41. The process of claim 6 wherein the strong acid is 10% oleum.

* * * * *